(12) United States Patent
Tom et al.

(10) Patent No.: US 6,295,861 B1
(45) Date of Patent: Oct. 2, 2001

(54) QUARTZ CRYSTAL MICROBALANCE SENSORS AND SEMICONDUCTOR MANUFACTURING PROCESS SYSTEMS COMPRISING SAME

(75) Inventors: Glenn M. Tom, New Milford; Mackenzie E. King, Newtown, both of CT (US)

(73) Assignee: Advanced Technology Materials, Inc., Danbury, CT (US)

(*) Notice: Subject to any disclaimer, the term of this patent is extended or adjusted under 35 U.S.C. 154(b) by 0 days.

(21) Appl. No.: 09/238,852

(22) Filed: Jan. 28, 1999

(51) Int. Cl.[7] .................. G01N 29/02; G01N 27/416; B01D 53/02
(52) U.S. Cl. .................. 73/24.06; 95/140; 436/151
(58) Field of Search .................. 73/24.06, 23.21, 73/658; 436/73, 151, 136; 428/411.1, 332, 327; 95/140

(56) References Cited

U.S. PATENT DOCUMENTS

| | | | |
|---|---|---|---|
| Re. 35,544 | 7/1997 | Snow | 73/24.01 |
| 3,427,864 | 2/1969 | King | 73/29 |
| 3,534,585 | 10/1970 | Stephens | 73/29 |
| 3,744,296 | 7/1973 | Beltzer | 73/23 |
| 3,969,927 | * 7/1976 | Yoshida et al. | 73/658 |
| 4,056,803 | 11/1977 | White et al. | 340/15 |
| 4,163,384 | * 8/1979 | Blakemore | 73/24.04 |
| 4,399,686 | * 8/1983 | Kindlund et al. | 73/24.06 |
| 4,446,720 | 5/1984 | Sinclair | 73/23 |
| 4,447,493 | * 5/1984 | Driscoll et al. | 428/332 |
| 4,637,987 | * 1/1987 | Minten et al. | 436/151 |
| 4,646,066 | 2/1987 | Baughman | 340/540 |
| 4,677,078 | * 6/1987 | Minten et al. | 436/136 |
| 4,730,478 | * 3/1988 | Gedeon | 73/23.21 |
| 4,735,081 | 4/1988 | Luoma et al. | 73/23 |
| 4,860,573 | 8/1989 | Barendz et al. | 73/23 |
| 5,037,624 | 8/1991 | Tom et al. | 423/210 |
| 5,042,288 | 8/1991 | Vig | 73/24.001 |
| 5,056,355 | 10/1991 | Hepher | 73/24.03 |
| 5,065,140 | 11/1991 | Neuburger | 73/23.31 |
| 5,095,736 | 3/1992 | Fesler et al. | 73/23.2 |
| 5,120,505 | 6/1992 | Lowell, Jr. et al. | 422/58 |
| 5,138,869 | 8/1992 | Tom | 73/31.03 |

(List continued on next page.)

FOREIGN PATENT DOCUMENTS 06308008A   4/1994   (JP) .................. G01N/5/02

OTHER PUBLICATIONS

Levenson, Leonard, L., *Applications of Piezoelectric Quartz Crystal Microbalances*, Editor C. Lu & A. W. Czanderna, vol. 7, Elsevier 1984, pp. 198–203.

(List continued on next page.)

Primary Examiner—Hezron Williams
Assistant Examiner—Jay L. Politzer
(74) Attorney, Agent, or Firm—Robert A. McLauchlan, III; Oliver A. Zitzmann

(57) ABSTRACT

A sensor device for detecting the presence of a gas species in a gas environment susceptible to the presence of same. The sensor device may include a piezoelectric crystal coated with a sensor material having adsorptive affinity for the gas species, with an electric oscillator arranged for applying an oscillating electric field to the piezoelectric crystal to generate an output frequency therefrom indicative of the presence of the gas species when present in the gas environment, when the gas environment is exposed to the piezoelectric crystal. Another aspect of the invention involves a porous polymeric material that may be employed as a sensor material on a piezoelectric crystal sensor device, as well as a quartz microbalance holder that enables reactor gas monitoring. The sensor device alternatively may comprise an optical sensor arranged in a non-contaminating fashion in relation to the gas environment being monitored.

17 Claims, 4 Drawing Sheets

U.S. PATENT DOCUMENTS

| | | | | |
|---|---|---|---|---|
| 5,151,110 | * | 9/1992 | Bein et al. | 95/140 |
| 5,151,395 | | 9/1992 | Tom | 502/67 |
| 5,208,162 | | 5/1993 | Osborne et al. | 436/6 |
| 5,210,121 | * | 5/1993 | Hinterwaldner | 524/109 |
| 5,260,585 | | 11/1993 | Tom | 250/573 |
| 5,320,817 | | 6/1994 | Harwick et al. | 423/237 |
| 5,325,705 | | 7/1994 | Tom | 73/31.03 |
| 5,339,675 | | 8/1994 | DiLeo et al. | 73/24.04 |
| 5,385,689 | | 1/1995 | Tom et al. | 252/194 |
| 5,411,709 | | 5/1995 | Furrki et al. | 422/91 |
| 5,417,821 | | 5/1995 | Pyke | 204/153 |
| 5,445,008 | | 8/1995 | Watcher et al. | 73/24.06 |
| 5,476,002 | | 12/1995 | Bowers et al. | 73/24.01 |
| 5,518,528 | | 5/1996 | Tom et al. | |
| 5,573,728 | | 11/1996 | Loesch et al. | 422/90 |
| 5,652,433 | | 7/1997 | Ouwerkerk et al. | 257/1 |
| 5,661,226 | | 8/1997 | Bowers et al. | 73/24.01 |
| 5,705,399 | | 1/1998 | Larue | 436/501 |
| 5,783,152 | | 7/1998 | Nave | 422/82.06 |
| 5,817,921 | | 10/1998 | Tom et al. | 73/24.01 |
| 5,827,947 | | 10/1998 | Miller et al. | 73/24.06 |

OTHER PUBLICATIONS

Dunbar, R.A. et al., "Development of chemical sensing platforms on sol–gel–derived thin films: origin of film age vs performance trade–offs", Analytical Chem., vol. 68, Feb. 15, 1996, pp. 604–610.

Hlavy, J. and Gullbault G.G., "Detection of Hydrogen Chloride Gas in ambient air with a coated piezoelectric quartz crystal," Analytical Chem., vol. 50, No. 7., Jun. 1978, pp. 965–967.

Neuburger, G.G., "Detection of Ambient Hydrogen Chloride with a Zinc–coated piezoelectric crystal resonator operating in a frequency–time differential mode" Anal. Chem., 1989, vol. 61, pp. 1559–1563.

Karter, L., "NASA proposes zeolite coats for contamination monitoring", NASA Tech Briefs Nov. 1996.

"The Worlds First 8–Bit RISC MCU in 2n 8–Pin Package," Philips Semiconductors, Nov. 7, 1997, 12 pages.

"SA612A Double–Balanced Mixer and Oscillator," Philips Semiconductors, Nov. 7, 1997, 12 pages.

* cited by examiner

QUARTZ CRYSTAL MICROBALANCE SENSORS AND SEMICONDUCTOR MANUFACTURING PROCESS SYSTEMS COMPRISING SAME

BACKGROUND OF THE INVENTION

1. Field of the Invention

The present invention generally relates to sensors for detecting gaseous components in gaseous environments containing same, to novel sensing materials useful in such sensors, and to semiconductor manufacturing process systems comprising such sensors.

2. Description of the Related Art

In the field of semiconductor manufacturing, wafer substrates are processed in reactor vessels in a variety of unit operations, such as deposition of thin film materials, e.g., by metalorganic chemical vapor deposition (MOCVD), etching (of the wafer and/or microelectronic device structures fabricated thereon), plasma treatment, ion implantation, etc. In addition, the reactor vessel itself may be subjected to cleaning by operations such as chamber etching, solvent flow-through, and elevated temperature volatilization of deposits.

The aforementioned operational functions are typically conducted for a given amount of time, as opposed to determining an endpoint for the process step by monitoring of process parameters with appropriate instruments. Accordingly, there is an absence of real-time control of these operational functions. Such lack of real-time control results in process inefficiencies. Further, there are few available reliable and inexpensive methods to follow the progress of a reaction in the reaction vessel. Test wafer and exact process control are usually the approach employed to gate the time of a process step.

In application to plasma-based processes, the art recently has proposed the use of optical emission spectroscopy (OES) and radio frequency (RF) impedance monitoring to detect changes in a plasma above a wafer, to demarque the end-point of the plasma-based process. Such approaches have significant deficiencies in practice, however. OES systems are prone to fogging of the optical windows employed in such systems, with consequent signal loss. RF impedance systems are highly sensitive to all changes in the overall state of the process, not just those of particular interest. Further, both OES and RF impedance systems depend on the presence of a plasma for their respective signals.

There is therefore a need in the art for a chemically selective device that provides the capability of endpoint monitoring without requiring the presence of a plasma.

More generally, in the field of gas monitoring, the art has employed various gas component detectors. Examples include pyrometric sensors, infrared and spectrophotometric detectors, gas chromatographic analyzers, and piezoelectric microbalances including quartz microbalances (QMBs) and surface acoustical wave devices (SAWs).

In some systems, a multiplicity of QMBs are employed for sensing of components of a multi-component gas stream, wherein each of the QMBs is coated with a specific sensor coating having affinity for a selected component or group of components of the multicomponent gas stream. In other instances, a single QMB may be used for detecting a single critical component of a multi-component gas stream.

A problem with the use of such QMB systems is that the means used to hold the crystal element(s) in position in the sensor device assembly are not very robust physically, and are not intended to be used in harsh environments, e.g., corrosive or otherwise chemically reactive atmospheres. Presently employed componentry typically uses glass to metal seals, steel wire, and silver epoxy for effecting electrical contact to the QMB element. All of such components fail in prolonged service in harsh environments.

It therefore would be an advance in the art to provide a holder or support structure for QMB elements that overcomes the aforementioned deficiencies.

In the art of QMB technology, it is known to coat a QMB element with a porous matrix coating, to provide an open material structure for interaction with gas component(s) of a gas stream or gas environment contacted with the QMB element. U.S. Pat. No. 5,827,947 issued Oct. 27, 1998 to Cindy Miller, et al. for "PIEZOELECTRIC SENSOR FOR HYDRIDE GASES, AND FLUID MONITORING APPARATUS COMPRISING SAME" discloses a sensor for detection of a trace fluid component in a fluid environment, comprising a piezoelectric crystal having a fundamental resonant frequency in response to an applied oscillating electric field, and an inert porous material coating on the piezoelectric crystal. The inert porous material coating contains a metal species that is reactive with the trace fluid component to yield a solid interaction product of changed mass in relation to initial mass of the metal species interacting with the trace fluid component to yield the solid interaction product.

It would be an advance in the art to provide an improved porous film material for use in forming an affinity coating on a QMB surface, for gas sensing applications.

It is an object of the present invention to provide sensing means, device structures and systems that in various embodied forms overcome the above-mentioned deficiencies of the prior art.

It is another object of the present invention to provide improved quartz crystal microbalance sensors for detecting gaseous components in gas mixtures containing same.

It is a further object of the invention to provide an improved semiconductor manufacturing process system comprising one or more QMB sensors.

Other objects and advantages of the invention will be more fully apparent from the ensuing disclosure and appended claims.

SUMMARY OF THE INVENTION

The present invention relates to sensors for monitoring a gaseous environment to detect the presence of one or more particular species therein, to novel sensing materials useful in such sensors, and to process systems comprising sensors for detection of gas components and for monitoring the process being carried out in the system.

In one aspect, the invention relates to a sensor assembly for detecting the presence of a gas species in a gaseous environment susceptible to the presence of the gas species. The sensor assembly comprises a housing including a chamber containing a piezoelectric crystal coated with a sensor material having a sorptive affinity for a species of the gaseous environment, wherein the piezoelectric crystal is arranged to interact with the gaseous environment in monitoring a compositional character of the gaseous environment.

In a specific embodiment of such sensor, two or more piezoelectric crystals are coated with different sensor material, so that each sensor material has a different sorptive interaction with the gaseous environment in exposure thereto. For example, each piezoelectric crystal may be coated with a different sensor material, so that each sensor material is sorptively selective for a different component of the gaseous environment.

In another aspect, the invention relates to a semiconductor manufacturing system, comprising a reactor arranged for discharging a gas stream; and a sensor assembly arranged to receive the gas stream discharged from the reactor and to detect the presence of a gas species in the gas stream susceptible to the presence of the gas species, such sensor assembly comprising a housing including a chamber containing a piezoelectric crystal coated with a sensor material having a sorptive affinity for a species of the gas stream, wherein the piezoelectric crystal is arranged to interact with the gas stream in monitoring a compositional character of the gas stream.

Another aspect of the invention relates to a high temperature composite manufacturing system, comprising an atmospheric pressure chemical vapor deposition reactor arranged for atmospheric chemical vapor deposition of ceramic coatings on reinforcement yarns to produce high temperature composite articles, and for discharging an effluent gas stream; and a sensor assembly arranged to receive the effluent gas stream discharged from the atmospheric pressure chemical vapor deposition reactor and to detect the presence of a gas species in the effluent gas stream susceptible to the presence of the gas species, such sensor assembly comprising a housing including at least two chambers each containing a piezoelectric crystal coated with a sensor material having a sorptive affinity for a species of the effluent gas stream, wherein each piezoelectric crystal is arranged to provide a different interaction with the effluent gas stream in monitoring a compositional character of the effluent gas stream.

In yet another aspect, the invention relates to a gas monitoring system, comprising: a main gas flow passage including an interior volume for flow of a gas stream therethrough; a first gas flow passage extension including an interior volume communicating with the interior volume of the main gas flow passage, such first gas flow passage extension comprising a window arranged to permit passage of sensing energy through the window and the interior volume of the first gas flow passage extension to the interior volume of the main gas flow passage; a second gas flow passage extension including an interior volume communicating with the interior volume of the main gas flow passage, such second gas flow passage extension comprising a window arranged to permit passage of sensing from the interior volume of the main gas flow passage through the interior volume of the second gas flow passage extension and the window of the second gas flow passage extension; a sensing energy source arranged to emit a beam of sensing energy and pass such beam of sensing energy through the window of the first gas flow passage extension and through the first gas flow passage extension to the interior volume of the main gas flow passage for impingement on the gas stream; a sensing energy receiver arranged in proximity to the window of the second gas flow passage extension, for receiving sensing energy passing from the interior volume of the main gas flow passage through the interior volume of the second gas flow passage extension and the window of the second gas flow passage extension; and a shrouding gas supply arranged to flow shrouding gas through the first and second gas flow passage extensions to oppose contact of the gas stream with the windows of the first and second gas flow passage extensions.

In another aspect, the invention relates to a method of monitoring a gas stream to determine a compositional characteristic thereof, comprising impinging sensing energy on the gas stream through a first window, detecting energy deriving from interaction of the sensing energy with the gas stream, through a second window; determining a compositional characteristic of the gas stream from the detected energy; and shrouding the windows with shrouding gas to oppose contact of the gas stream with the windows.

A still further aspect of the invention relates to a quartz microbalance holder, comprising an enclosure formed of a polymeric material that is chemically inert to corrosive gas, such enclosure having at least one positioning slot for securement of a quartz microbalance crystal therein; and contacts for electrical connection of the quartz microbalance crystal, said contacts comprising an external surface formed of a metal that is inert the corrosive gas.

Another aspect of the invention relates to a quartz microbalance assembly, comprising (I) a quartz microbalance holder, including an enclosure formed of a polymeric material that is chemically inert to hydrogen fluoride, such enclosure having at least one positioning slot for securement of a quartz microbalance crystal therein; contacts for electrical connection of the quartz microbalance crystal, said contacts comprising an external surface formed of a metal that is inert to hydrogen fluoride; and (II) a quartz microbalance crystal positioned in a positioning slot of the enclosure, and in electrical connection with said contacts.

Another aspect of the invention relates to a method of making a porous polymeric material, comprising formulating a material precursor composition including a solvent solution or suspension containing starting materials for forming an interpenetrating network of at least two polymers A and B, such starting materials being selected from the group consisting of (i) polymer A; (ii) monomer A polymerizable to form polymer A; (iii) polymer B; (iv) monomer B polymerizable to form polymer B; and (v) combinations of the foregoing; forming a mass comprising the interpenetrating network of at least two polymers A and B from the material precursor composition including polymerization of monomer(s) in the material precursor composition, and removal of solvent from the composition; and treating the mass to remove part of the polymeric material therein, to yield the porous polymeric material.

In a specific embodiment of such method, the porosity of the porous polymeric material is back-filled with a different material to form a composite product material, e.g., wherein one of the porous polymeric material and the aforementioned different material is ionically conductive and the other is electrically conductive, to form a composite electrode.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
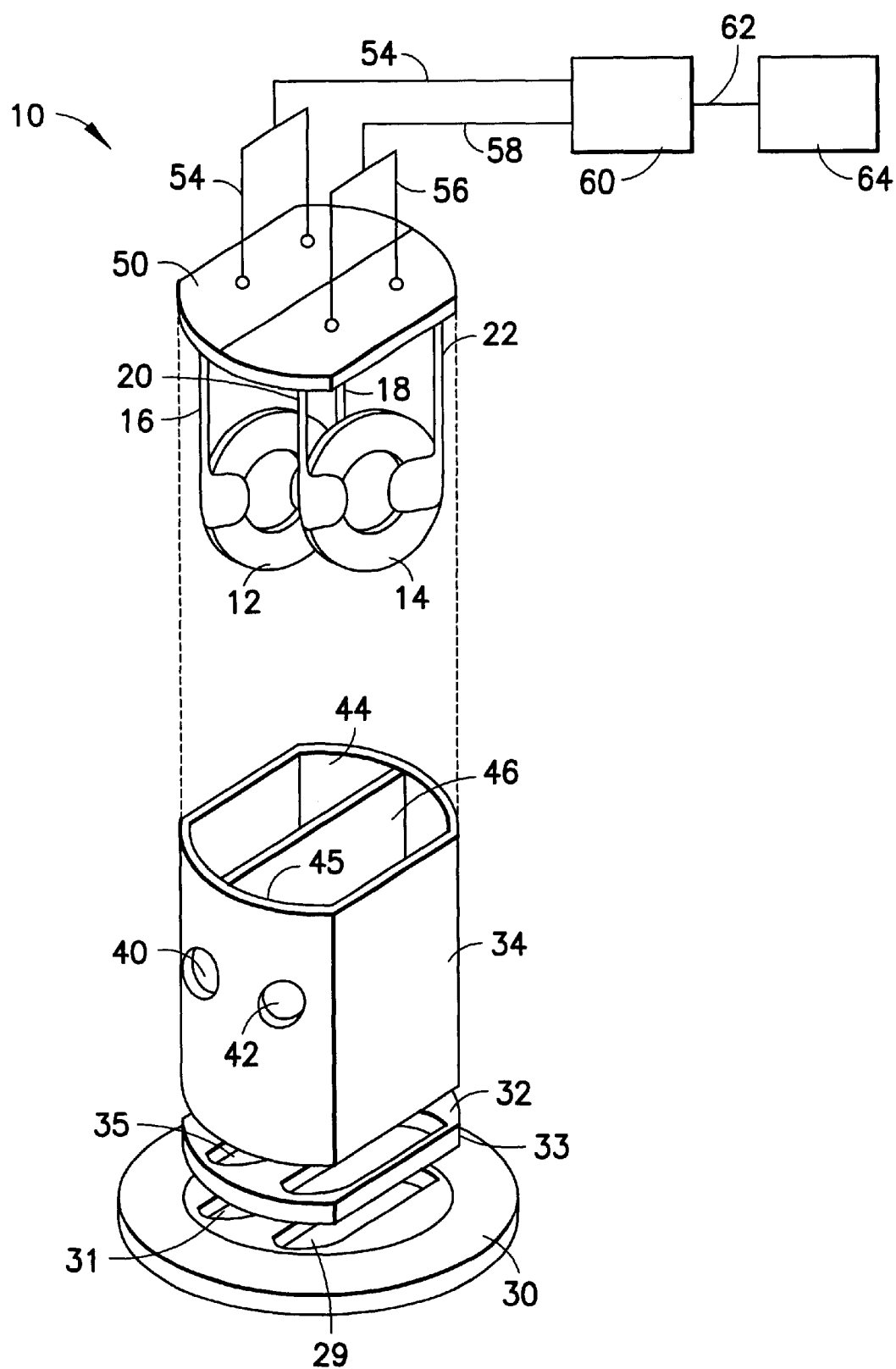
FIG. 1 is a schematic representation of a quartz crystal microbalance detector assembly according to one embodiment of the invention.

The disclosure of United States patent application Ser. No. 08/785,342 filed Jan. 17, 1996 in the names of Glenn M. Tom and Cynthia A. Miller for "Piezoelectric Sensor for Hydride Gases, and Monitoring Apparatus Comprising Same," and issued Oct. 27, 1998 as U.S. Pat. No. 5,827,947, is hereby incorporated herein by reference in its entirety.

The QMB sensors employed in the practice of the invention utilize a quartz crystal having coated on the surface thereof a coating of sensor material. The sensor material has a sorptive affinity for the gas component(s) of interest, and may for example be selected to be specifically physically adsorptive for a single component of a multi-component gas mixture, e.g., in a gas stream flowed in contact with the QMB sensor.

In operation, an electrical oscillation is imposed on the QMB sensor to produce a frequency response that will vary from the fundamental frequency of the QMB sensor (the fundamental frequency being the frequency response that is generated by the imposed signal in the absence of any sorption of gas species on the coated crystal surface) when the gas species of interest interacts with the sensor material. The sensor material interacts with the gas to adsorb the component(s) of interest, producing a mass change of the coating (now having the gas species associated therewith), so that the frequency response is altered from the fundamental frequency. The change in frequency can be quantitated to reflect the concentration of the sorbed gas species in a volume or stream of gas. Alternatively, the rate of change of the frequency response can be monitored and used to quantitate the concentration on a dynamic real-time basis, where the gas-phase concentration of the species of interest is highly time-variant in character.

In some instances, in lieu of using a physical adsorbent coating on the QMB sensor, it may be desirable to employ a chemisorbent material for the gas species of interest, to reactively form an interaction product by interaction of the gas species with the chemisorbent coating material, which is of a different mass that the original coating material. Such difference of mass of the sensor coating incident to reaction then can be employed to determine the presence and concentration of the gas species of interest.

It will be appreciated from the foregoing as well as the ensuing disclosure that the piezoelectric crystal sensors of the invention may be variously configured, arranged and operated. The piezoelectric crystal sensors will be described hereinafter with primary reference to QMB devices, but it will be appreciated that the sensor may alternatively or additionally comprise SAW devices as the active sensing means.

In one aspect, the invention relates to the implementation of multiple high surface area thin film polymer species on multiple microbalances (QMBs) to achieve selective gas adsorption and desorption for a manufacturing process. Such approach utilizes chemically distinct polymer materials whose adsorptive properties for each gas differs, thereby permitting selective adsorption of a gaseous species while the microbalance allows the amount of a species to be quantitated.

Additionally, cooling and heating of the microbalances may be employed to enhance the adsorption/desorption processes. The physical adsorptive affinity of the sensor coating on the QMB crystal surface is a function of temperature, and the sorptive loading of a physically adsorptive material generally increases with decreasing temperature, and decreases with increasing temperature.

When cross-referenced with the mass change from other selective films the amount and type of gaseous species may be identified. An array of QMBs may be employed to enable analysis of multi-component effluents from process environments. The microbalance array may be located in any atmosphere, e.g., at pressures in the range of from 800 torr down to millitorr levels.

Heating and cooling of the microbalances facilitates selective adsorption of one gas species over another. Cooling the QMB will increase the "sticking" probability of a gas molecule on the surface of the sensor material, while heating will accelerate the rate at which adsorption and desorption from the film occurs.

Illustrated in FIG. 1 is a quartz microbalance sensor assembly 10 which uses two QMBs 12 and 14 whose temperatures are independently regulated in each respective chamber 44 and 46 of housing 34. The chambers 44 and 46 are defined in the interior volume of the housing by partition 45. One of the chambers 44 and 46 may be selectively cooled in relation to the other chamber, to make detection of higher vapor pressure gases easier by suitable thermal adjustment and monitoring means (not shown).

The sensor assembly 10 includes the aforementioned QMBs 12 and 14 mounted on the end plate 50 which cooperatively mates with the housing 34, being bonded, mechanically fastened or otherwise secured thereto, so that the QMB element 12 is disposed in chamber 44, and the QMB element 14. The QMB element 12 is joined by leads 16 and 18 to associated exterior lead assembly 52 and signal transmission line 54 to processing circuitry in the electronics module 60. Likewise, the QMB element 14 is joined by the leads 20 and 22 to associated exterior lead assembly 56 and signal transmission line 58 to the processing circuitry in the electronics module 60.

The processing circuitry in the electronics module 60 includes oscillator circuitry and signal processing circuitry for applying an oscillating electric field to the piezoelectric crystal that generates an output resonant frequency therefrom, sampling the output resonant frequency of the piezoelectric crystal while the oscillating electric field is applied thereto, determining the change in resonant frequency, or the rate of change of resonant frequency, incident to the interaction of the sensor material with the gas species of interest, and generating an output indicative of the presence of the gas species of interest in the gas mixture being monitored.

The output from the electronics module is passed by signal transmission line 62 to the process monitoring and feedback module 64. Module 64 may include visual display means such as a monitor, recorder, flashing light or colorimetric alarm, etc. to provide a visually perceivable indication of the presence and/or concentration of a particular gas species in the gas mixture being monitored by the system. Module 64 may also include audio alarms for output reflecting the presence of a particular gas species in the monitored gas mixture, or other output or display means for such purpose.

Further, the module 64 may comprise adjustment or modulating means for adjusting a process or source of the gas mixture, to obtain a desired concentration level of a particular gas species in the multi-component gas mixture, or for effecting a change in the treatment of a gas mixture to abate a particular gas species therein.

For example, the gas mixture may comprise a multi-component gas stream that is flowed into the housing 34 to permit sensing of specific components by the QMB elements in the respective chambers 44 and 46. In response, an upstream process system producing the gas stream may be moderated by feedback from the module 64, to adjust the process conditions (e.g., pressures, temperatures, flow rates, compositions, etc.) of the upstream process so that it yields a product gas stream of the desired character.

For purposes of monitoring the respective components of a multi-component gas mixture in the housing chambers 44 and 46, and independently adjusting the temperature and pressure of the respective chambers, the housing 34 is provided with pressure/temperature monitoring ports 40 and 42, which accommodate the coupling with the housing of suitable means (not shown) for monitoring the pressure and/or temperature of a chamber, for cooling or heating a chamber for a specific gas component sensing, etc.

The lower end of the housing 34 of the sensor assembly 10 mates with thermal insulating gasket 32 having openings 33 and 35 therein, with the gasket in turn mating with adapting flange 30 having openings 29 and 31 therein, so that the opening 29 of the adapting flange 30 is in register with opening 33 of gasket 32, and the registered openings 29 and 33 are in gas flow communication with the chamber 46 of the housing 34. Concurrently, the opening 31 of the adapting flange 30 is in register with the opening 35 of the gasket 32, and the registered openings 31 and 35 are in gas flow communication with the chamber 44 of the housing 34.

The flange 30 may be connected to a piping fitting, to a conduit or to a process chamber of an industrial facility, to permit the gas mixture to be monitored to permeate through the registered openings to the QMB elements in the respective chambers for detection of specific gas components therein.

In this manner, the gas mixture being monitored can be sensed in each of the two chambers 44 and 46, e.g., with different sensor coating materials on each of the respective QMB elements so that different components of the gas mixture are able to be monitored. Alternatively, the gas mixture can be simultaneously monitored in the respective chambers at different conditions, e.g., different temperature conditions. For this purpose, the partition 45 as well as the gasket 32 may be formed of a thermal insulating material, and the housing 34 itself may be formed of a material having suitably low thermal conductivity.

It will be appreciated that the QMB assembly of the invention may be arranged with more than two QMB elements, each in a separate chamber, so that more than two components of the gas may be individually monitored, and/or so that the gas mixture may be monitored under a variety of sensing conditions.

Alternatively, the QMB assembly may be arranged with only a single QMB element, but with the element being subjected to exposure to different gas flows at different times, e.g., by means of a cycle timer program controlling valves in flow circuitry including different gas flow streams, so that gas is sampled and contacted with the QMB element at predetermined intervals or in a predetermined sequence.

Accordingly, it will be appreciated that the QMB assembly of the invention may be alternatively configured, arranged and operated, in a wide variety of differing embodiments.

As an illustrative embodiment of the invention, the QMB assembly may incorporate an array of two microbalances each coated with a high surface area polymer (polystyrene sulfonic acid, and polyvinyl chloride vinyl acetate copolymer, respectively). Both the microstructure and the chemistry of the QMB sensor coating influence adsorption of gaseous species thereon. In semiconductor manufacturing, high density plasma chamber cleaning operations using $NF_3$ is carried out after chemical vapor deposition processes.

Such plasma cleaning operation produces an effluent that contains HF and $SiF_4$, which adsorb selectively on the high surface area polymer films. The polystyrene sulfonic acid responds to both gases while the polyvinyl chloride responds to primarily HF only. By monitoring the adsorption and subsequent desorption of these species at the polymer film involving a change in crystal frequency, a direct correlation to the partial pressure of each of the gaseous species may be made. Thus, if attenuation of the HF partial pressure signals the end of an etch process the microbalance array will register a reduced HF mass on the polymer films (corresponding to an increase in frequency) which in turn tells the operator of the process to terminate the etch operation in a manual control system, or the increase in frequency may be employed to actuate an automatic controller to terminate the cleaning operation.

A second illustrative example of an embodiment of the present invention uses a similar array to that used above but the process being monitored is a chamber cleaning operation following deposition of tungsten in the reactor chamber of a semiconductor manufacturing facility. In such embodiment, $NF_3$ is used in conjunction with a plasma to create fluorine radicals that react with tungsten on the chamber walls to form the gaseous species $WF_6$ and HF. Again, the partial pressure of the gaseous species of interest may be monitored through the frequency changes of the crystal due to adsorption and desorption of the gaseous species at the sensor coating polymer films.

A third illustrative example uses a two crystal array to monitor the etching of $SiO_2$ from the chamber walls using anhydrous HF gas. The formation and subsequent attenuation of $SiF_4$ in the vapor phase is indicative of the state of the chamber walls (as regards the amount of $SiO_2$ thereon). The adsorption of $SiF_4$ and other species onto the polymer thin films on the microbalances can be closely monitored through frequency changes of the crystals, and such frequency change can be related to the gas phase concentration of the species. The endpoint of the etch process may therefore be determined by a sensed decrease in $SiF_4$ concentration.

A fourth illustrative example demonstrates how the QMB assembly may be protected from exposure to species that are not to be monitored or that are considered detrimental to the QMB elements of the assembly. If the QMB assembly is used to monitor a CVD process using a CVD precursor or dopant such as TEOS or phosphine, then the microbalance device would be susceptible to the gaseous environment in a manner that may alter the adsorptive properties of the polymer films.

To guard the system against this possibility the microbalance array may be arranged in a housing that incorporates gas inlet ports for the introduction of an inert carrier gas, to provide a shield against unwanted molecular species adsorbing onto the sensor coating films. Upon completion of the process using the undesirable reagent the carrier gas flow to the microbalances may be terminated, and normal flow contacting of the QMB element(s) with the gas mixture may be resumed.

For example, the ports 40 and 42 in the sensor assembly of FIG. 1 may be modified so that an inert shrouding gas is flowed through such ports during the period of operation that the gas stream otherwise being sensed contains the undesirable component that in contact with the microbalance sensor coatings would adversely affect such coatings. When the undesirable component is no longer present in the gas stream, such flow of inert shrouding gas through the ports 40 and 42 is terminated to again allow the gas stream to contact the microbalance crystals and the sensor coatings thereon, to reinitiate the active sensing operation.

A fifth illustrative example utilizes a reactor gas monitor in atmospheric pressure chemical vapor deposition (APCVD) of ceramic coatings on reinforcement yarns for the manufacture of high temperature composites. Application of the APCVD reagent to the yarn produces byproducts such as $CO_2$, water, and various alcohols. A QMB sensing assembly may therefore be provided with a third and fourth sensor employing siloxane and polyethylene oxide coatings to permit real-time quantitation of the gases in the effluent gas stream, and the implementation of process control in the APCVD system.

The sensor assembly in the practice of the invention may be arranged as illustratively shown in FIG. 1, with the microbalance crystal elements being located within the chambers of the sensor assembly, and oriented parallel to the major axis of the chamber, or in any other suitable manner necessary or appropriate in the specific end use application of the invention being practiced.

In QMB sensors according to the present invention, having an affinity coating on the surface of the crystal, the affinity coating desirably is as thin as possible, in order to provide the required sensitivity without undue "damping" of the frequency response of the crystal, since thicker films of coated material present diffusional barriers to full utilization of the coating material in the interior of the film, as well as deviations from the desired region in proximity to the fundamental harmonic frequency of the crystal.

For such purpose, the sensor material film may be continuous or discontinuous in character, depending on the density of the "active" sites provided for interaction with the gaseous component(s) that may be present in the environment being monitored by the sensor device.

By way of example, the coating of material that is interactive with the gaseous component(s) present in the environment being monitored may be deposited on the crystal surface by techniques such as solution deposition methods, vapor deposition, spraying, dip coating, roller coating, etc.

The amount (surface loading) of the coating material may be readily determined without undue experimentation by the simple expedient of coating piezoelectric crystals with different surface loadings of the sensor coating material and then measuring the frequency response and sensitivity characteristics of the coating at an illustrative concentration level (of the component(s) to be sensed by the sensor) that is chosen to simulate the environment to be monitored in the use of the sensor device.

As mentioned, the thinner the coating material on the crystal, the more highly sensitive the coating material, provided that an adequate number of interaction sites is provided for the material to reproducibly register a significant interaction with the component(s) in the environment being monitored.

The coating material used in the practice of the invention may be directly applied to the surface of the piezoelectric crystal, or it may be applied in a suitable binder or matrix material. For example, the piezoelectric crystal may be coated with a sol gel matrix coating, containing the active sensing component. Sol gel coatings of such type are more fully described in the aforementioned U.S. Pat. No. 5,827, 947.

To maintain a constant flow of the sensed fluid medium to the sensor element and to avoid contamination of the sensor element with particulates, a frit or a flow restrictor may be deployed in a gas flow passage, e.g., conduit, through which the gas being sampled is flowed. Such flow restriction means may be employed to force the flow to be purely or substantially diffusional in character, and it will act as a particle filter at the same time, so that the gas flow passage is not clogged in use.

It is generally suitable in the broad practice of the invention to fabricate and operate the QMB sensor such that the coated piezoelectric crystal exhibits a frequency response rate to the gas component to be detected, that is in the range of from about 0.001 to about 100,000 milliHertz/min/(part-per-million of the gas component), preferably in the range of from about 0.01 to about 10,000 milliHertz/min/(part-per-million of the gas component), more preferably in the range of from about 0.1 to about 5,000 milliHertz/min/(part-per-million of the gas component), and most preferably in the range of from about 1 to about 1000 milliHertz/min/(part-per-million of the gas component). Such arrangement may entail the sampling by the coated piezoelectric crystal of a slip-stream or side-stream of a main flow of a main gas stream, or the restricted access of the main flow of the gas stream to the coated piezoelectric crystal.

The electronics module output associated with the piezoelectric crystal may comprise a liquid crystal display, monitor or other visual output means, which may numerically display a concentration value or other information for the gas species being monitored. Alternatively, the output means may provide a colorimetric display, e.g., with red indicating a hazardous or dangerously high concentration of the monitored gas component, yellow indicating a tolerable but high concentration of the gas component, and green indicating that the gas component concentration is within acceptable concentration limits. As still other alternatives, the output means may comprise an audible alarm, other visual display (e.g., a flashing light), or any other suitable output means.

The electronics module associated with the QMB sensor may be suitably constructed and arranged for (i) sampling the output resonant frequency of the piezoelectric crystal while the oscillating electric field is applied thereto, (ii) determining the change in resonant frequency from the fundamental resonant frequency that occurs on formation of the solid interaction product when the sensor material interacts with a specific gas species in the sampled gas stream, and (iii) generating an output indicative of the presence of the gas species in the gas stream, with the coated piezoelectric crystal exhibiting a frequency response rate to the gas species, that is in the range of from about 0.001 to about 1000 milliHertz/min/(part-per-million of the gas species).

The sensor element of the invention thus may comprise a piezoelectric crystal that is coated with a suitable material for interacting with the gas species of interest, to yield an interaction product of differing mass characteristic than the original coating material.

In one embodiment of the invention, the sensor device may be coupled with a reference device that is supplied with or exposed to a same gas as the main sensor device, but which has been purged of any content of the gas species of interest, so that a "base" reference is provided for comparative generation of an output indicative of the presence of the gas species of interest in the gas mixture that is contacted with the main sensor device. Appropriate comparator circuitry may be used in the electronics module for such purpose.

It will be appreciated that the sensor device of the invention may assume a wide variety of conformations and arrangements in the broad practice of the invention, consistent with the specific end use of the sensor device, and the nature and extent of the output function thereof.

Figure 2:
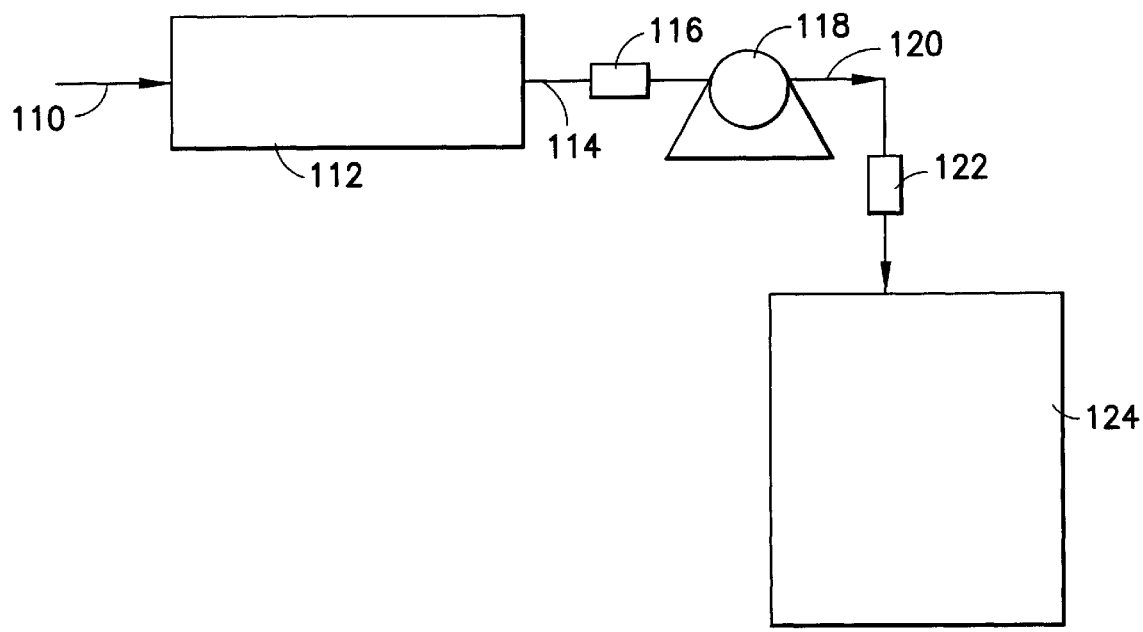
FIG. 2 is a schematic representation of a process system according to another embodiment of the invention, wherein an optical detector is arranged to detect the presence a specific component in the process stream discharged from a reactor vessel in the system.

FIG. 2 is a schematic representation of a process system according to another embodiment of the invention, wherein an optical detector is arranged to detect the presence a specific component in the process stream discharged from a reactor vessel in the system. The embodiment of FIG. 2 employs an optical detector to measure an analyte from the process, wherein the concentration of the analyte provides a measure of the progress of a processing or cleaning step being carried out in a reactor in the process system.

For example, the process may comprise a cleaning step in a semiconductor manufacturing facility, in which the analyte is constituted by particles that are removed from the walls of a reactor vessel by passage through the vessel of an etching medium. In other processes, the analyte may be a specific molecule such as $SiF_4$.

In this embodiment, the sensor comprises an optical measuring device. Optical measurements have the advantage of avoiding the contact of the process stream (being monitored) with the detector device, and thus are suitable for use in harsh environments such as those encountered in reactor vessels of semiconductor manufacturing operations.

As illustrated in FIG. 2, the process system includes a reactor vessel 112 that receives a process stream in line 110. The process stream may for example be a metalorganic source reagent in the case of metalorganic chemical vapor deposition (MOCVD), or alternatively, the process stream may be an etching agent that is passed through the reactor to etch and effect removal from the reactor walls of solid deposits from a prior MOCVD operation.

In any event, the reactor 112 discharges a process effluent in line 114, which is coupled to the pump 118. The pump 118 may be arranged to overcome the pressure drop in the system and to discharge the effluent gas stream into line 120, in which the effluent gas stream is flowed to treatment complex 124.

The treatment complex 124 may comprise a gas scrubbing system or other complex for carrying out unit operations as necessary for abatement of selected components of the effluent gas stream. Such unit operations may for example comprise incineration, catalytic oxidation, pH adjustment, chemical reaction, fluid contacting, physical adsorption, chemisorption, etc., as necessary or desirable for treatment of a given effluent gas stream.

The optical sensing device that is used in the FIG. 2 system may comprise a sensor 116 upstream of the pump 118, or a sensor 122 downstream of the pump 118. Because of its proximity to the reactor 112, the position of sensor 116 affords a more direct measurement of the gas stream, which may be preferable to the position of sensor 122. Additionally, the position of sensor 122 will introduce delays to the measurement (due to the longer run of piping from the reactor) as well as possible introduction of trace contaminants such as oil or other lubricant from pump 118 into the gas stream.

In use of the FIG. 2 system for controlling the process step of cleaning of the reactor 112 with an etching agent, the generation of particles from the etching operation will decrease when the etch cleaning is approaching completion. Thus, the number of particles in the effluent stream from the reactor will change in the course of the cleaning operation.

The optical sensor can therefore be used to measure light scattering by particles incident to impingement of a light beam, e.g., a laser beam of coherent light, on the particles in the effluent gas stream. The scattered light intensity is proportional to the concentration of the particles in the effluent gas stream, at low particle concentrations. The optical sensor can therefore be employed as an end-point sensor for etch cleaning of the reactor.

A fundamental problem with the use of such optical sensing techniques is the potential for coating of the optics by the particles themselves as well as other forms of contamination deriving from the effluent gas stream.

Figure 3:
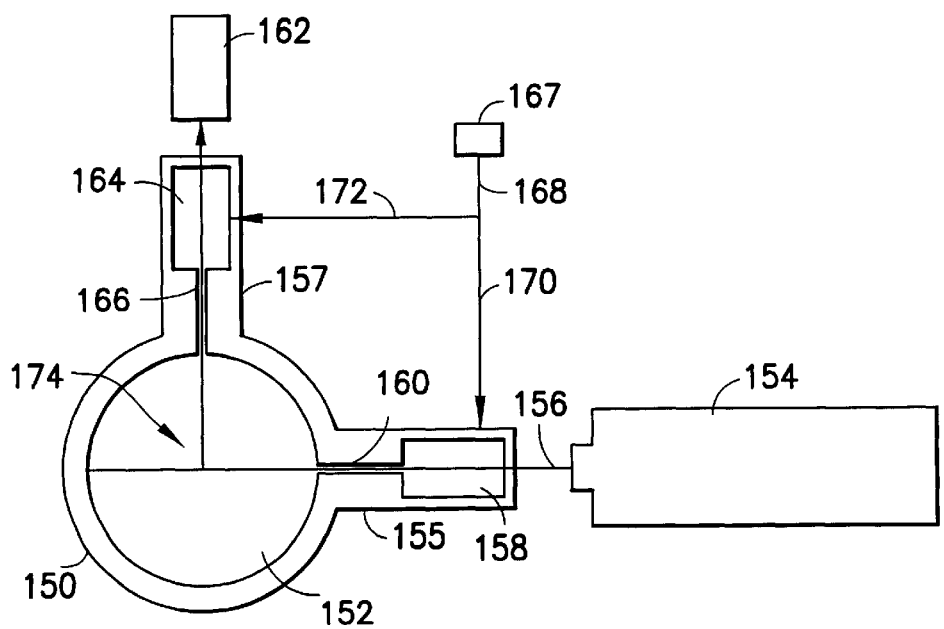
FIG. 3 is a schematic representation of a photodetection system embodying another aspect of the invention.

FIG. 3 is a schematic representation of a photodetection system embodying another aspect of the invention, which obviates the aforementioned fouling problem.

In the FIG. 3 system, a gas stream is flowed through the interior passage 152 of a flow conduit 150. The flow conduit 150 has a first radial extension 155 having a cavity 158 therein communicating with the interior passage 152 though extension constriction 160. A laser 154 is arranged to emit a beam of coherent light 156 that passes through the cavity 158 and constriction 160 into the interior passage 152.

The flow conduit 150 has a second radial extension 157 that is similarly constructed with an interior cavity 164 communicating with the interior passage 152 through extension constriction 166.

At the outer extremity of each of the extensions 155 and 157 is an optical window to accommodate the transmission of light therethrough, as hereinafter more fully described.

The laser beam 156 in the interior passage 152 produces a scattered beam 174, resulting from impingement of the beam on a particle in the interior passage 152, that then passes through the constriction 166 and cavity 164 to the photo receiver 162.

It will be appreciated that other forms of energy may be potentially employed in place of a laser beam 156, e.g., non-coherent light sources, ultrasonic energy sources, electron beam sources, x-ray sources, etc.

The photo receiver 162 used in the practice of the invention may comprise a photodiode detector, a charge-coupled device (CCD) detector, a scintillation detector, or any other suitable detector that is appropriate to the energy source that is being employed for impingement on the gas stream flowing through the gas flow passage in which the gas stream is being monitored.

A source 167 of an inert gas supplies inert gas into the line 168, from which the flow is split and passed in line 170 to the cavity 158 at a low flow rate that is sufficient to avoid the fouling of the window at the outer extremity of the extension 155, and in line 172 to the cavity 164 at a low flow rate that is likewise sufficient to avoid the fouling of the window at the outer extremity of the extension 157.

By this arrangement, the low "bleed" of inert gas is flowed through the respective cavities and the associated constrictions into the interior passage 152 of the flow conduit 150, to thereby "shroud" the optical windows in the respective extensions and prevent their contamination from the gas stream flowing through the interior passage 152. The laser beam may therefore be impinged on the gas stream flowed through interior passage 152, to generate a scattering of light that may be sensed by the photo-receiver.

The dimensions of the extensions and interior passages therein (e.g., the length to diameter "L/D" ratio thereof) and the linear velocity of the inert gas is selected so that the effluent gas stream is prevented from contacting the windows at the extremities of the respective extensions, while providing interior passages that are large enough to avoid interference with the light beams passed therethrough.

The structural geometry and dimensional characteristics of the constrictions and cavities are important in avoiding the plugging of the gas and light paths in the system. Additionally, the flow of the inert gas through the respective extensions is selected so that the addition to the main gas flow of the effluent gas stream does not perturb the process.

Figure 4:
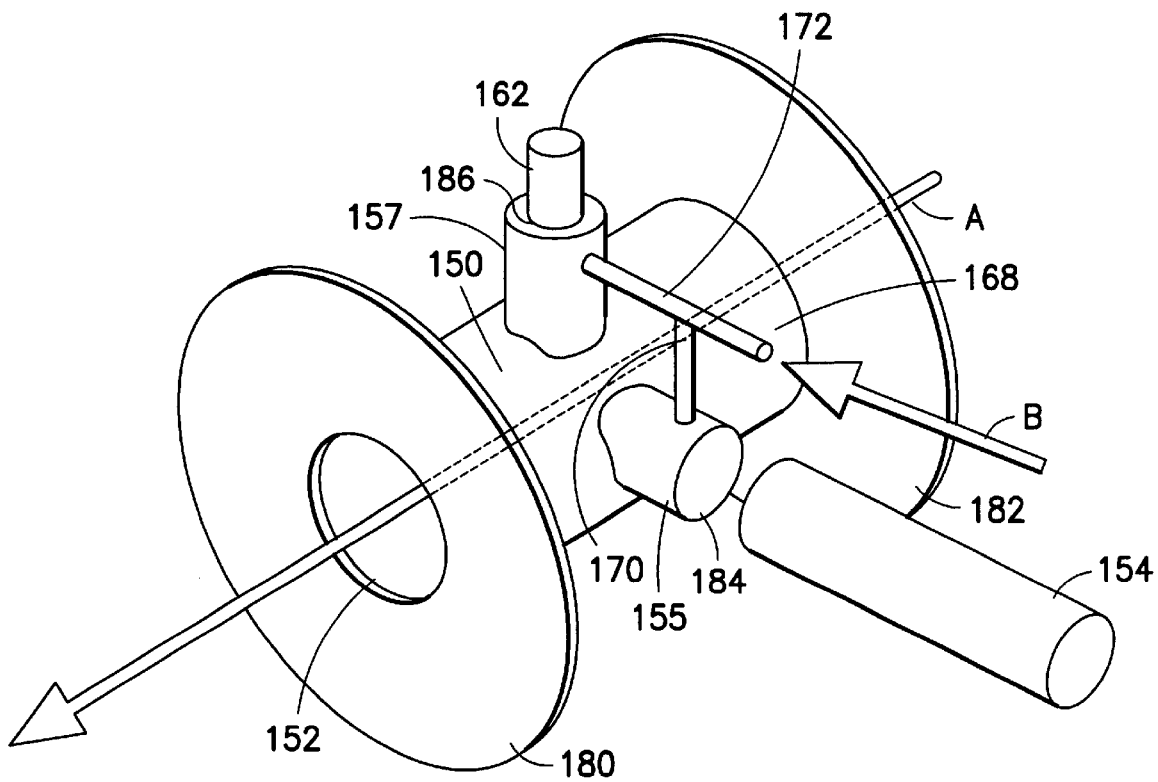
FIG. 4 is a perspective schematic representation of the photodetection system of FIG. 3.

The system of FIG. 3 is shown in a schematic perspective view in FIG. 4. The system elements and features are shown in FIG. 4 as correspondingly numbered to the same elements and features in FIG. 3. The flow conduit 150 as illustrated may comprise a conduit section with longitudinally spaced-apart terminal flanges 180 and 182 permitting the conduit 150 to be coupled with piping in a process facility. The arrow A shows the direction of flow of the effluent gas stream through the interior passage 152 of the conduit, and arrow B shows the direction of flow of the inert gas that is introduced to line 168 and used to purge the extensions 155 and 157. The optical window 184 of extension 155 and the optical window 186 of extension 157 are shown in the perspective view of FIG. 4.

In operation, the system of FIGS. 3 and 4 provides a measure of the change of particles in the effluent gas stream being monitored, and corresponding process signals can be generated for monitoring and control purposes. For example, in the aforementioned reactor vessel etch operation, the initial occurrence of scattering of the incident light beam could provide a process feedback signal indicative of the flow of etch gases, and use the initial light scattering level as a base line for the process. Comparison of the light scattering level in subsequent operation with the initial base line level permits operation in a manner that eliminates drift as a significant factor in process monitoring.

The optical monitoring system has been described above as being employed for the monitoring of particulate levels in the effluent gas stream. In other applications, the optical system of the invention may be utilized to detect specific component(s) of the gas stream flowed through the interior passage 152 by means of light absorption by the component (s) of interest. In such respect, the optical windows may be aligned in a straight line in relation to one another, and the purging of the extensions with an inert or other suitable gas is carried out as previously described to provide a controlled microenvironment in the vicinity of each optical window that prevents fouling of the window.

In a variant arrangement, series of optical detectors may be arranged along the gas stream flow conduit 150, each with light of a specific wavelength for which a separate component of the gas stream is adsorptive. In such manner, the presence and concentration of a multiplicity of gas components in the multi-component gas stream may be simultaneously monitored in real-time fashion.

Figure 5:
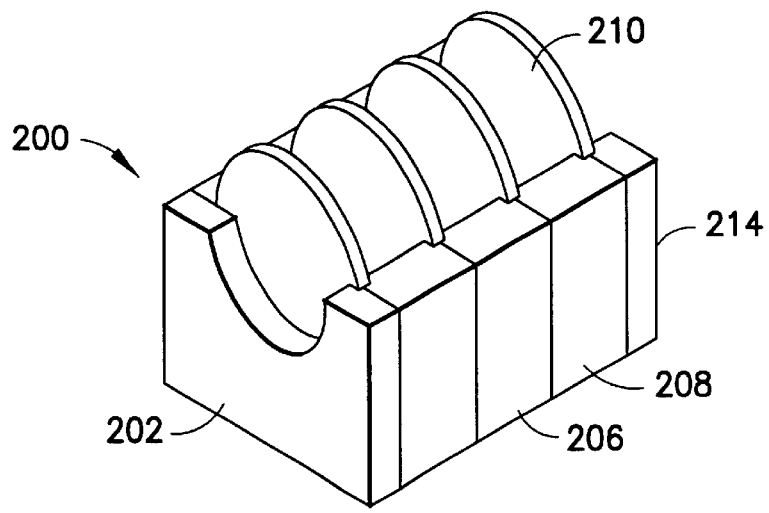
FIG. 5 is a perspective schematic view of a QMB holder according to another embodiment of the invention.

FIG. 5 is a perspective schematic view of a quartz microbalance holder 200 according to another embodiment of the invention.

As mentioned earlier herein, conventional devices used to hold quartz crystal microbalances are not meant to be used in harsh environments or corrosive atmospheres, since they utilize glass to metal seals, steel wire, and silver epoxy for electrical contact to the quartz microbalance element, which components fail in prolonged service in harsh environments.

The quartz microbalance holder 200 device is made of three components: endplates 202 and 204, a single crystal holder 206 and a dual crystal holder 208. The number of microbalance crystals 210 that can be retained in the holder is limited only by the number of single crystal holder modules that can be fit into the device being used.

In the holder 200, the endplates 202 and 204 are matably engageable or securable to the adjacent dual crystal holders, which are in turn each engageable or securable to the single crystal holder therebetween. Such connection may include tongue-and-groove or snap-lock elements or other complementary mating structures on the respective structural elements of the holder, or the structural elements may be bonded or welded to one another to form the holder structure, by any suitable joining or bonding technique.

The aforementioned holder elements are formed of a suitable material of construction, such as a polymeric material that is resistant to chemical attack. Examples include polyimide, polysulfone, and the like. A preferred material of construction for semiconductor manufacturing operations, in which the quartz microbalance is used for reactor chamber effluent gas monitoring, is polyimide.

The contacts (leads) used with the QMB elements are likewise formed of a material that is resistant to chemical attack, e.g., a noble metal composition, or a plating of such material on an otherwise structurally appropriate material element.

In one embodiment, the QMB holder module is made of polyimide with gold-plated or nickel-plated spring steel contacts for the electrical connection. For example, a 1000 Angstroms thick layer of gold is suitable for most corrosive applications, but other applications may require nickel plating. Both materials are compatible with corrosive and harsh environments. The spring contacts from the quartz crystals feed through the bottom of each fastening module to allow connection with suitable external oscillator driver circuits (not shown in FIG. 5).

As an example of a system employing the QMB holder of the invention, wherein the holder body is formed of polyimide components, and the contacts are formed of gold-plate steel, a CVD chamber etch process may be employed that utilizes HF or fluorine radicals (from plasma-dissociated $NF_3$) to etch metals and inorganics such as tungsten or $SiO_2$ from the chamber walls of a chemical vapor deposition reactor. In order to monitor the effluent of this process with a quartz crystal microbalance, the microbalance components must be compatible with HF, a highly corrosive gas. Typical glass-to-metal seals used for supporting the microbalance quickly react with the HF and become unstable as a mechanical support, but HF will neither corrode the gold-plated spring steel contacts nor affect the polyimide module.

As mentioned, the sensor material coating on the surface of a quartz crystal microbalance may be formed of a porous material to facilitate the nature and extent of interaction with gas phase component(s) with the sensor material film.

Another aspect of the present invention relates to a novel quartz crystal microbalance structure employing a porous polymeric film as the gas affinity structure or as a support matrix for impregnation with an active gas affinity component.

High surface area polymers exist primarily as mechanically-stabilized, cross-linked, macroscopic particles such as polystyrene divinylbenzene beads. Other methods of producing bulk porous polymers include rapid solvent evaporation such as may be done with supercritical fluids. Thin polymer films are typically spin-, dip-, or spray-coated and the resulting polymer network is relatively non-porous. Furthermore, adsorption kinetics are very slow.

The present invention overcomes the disadvantages inherent in the aforementioned polymeric films of the prior art, by a novel approach of forming a porous thin film (e.g., a layer of less than 300 nm thickness) from an interpenetrating polymer network (IPN).

IPNs are not a new technology and are currently being explored for the formation of composite organic/inorganic polymer structures. The present invention, however, utilizes IPN technology with a novel approach, in which one of the components of the IPN is dissolved away or otherwise removed from the structure to expose a porous network formed by the second component of the IPN.

The resulting porous structure is suitable for use as a matrix or support for sorbing gas components when utilized as an affinity coating on a piezoelectric crystal for gas sensing applications, or alternatively as a matrix or support medium for an active material having adsorptive or chemisorptive affinity for the gas species of interest.

In one embodiment of such aspect of the invention, two miscible monomers, and/or monomer and polymer, and/or two polymers, may be mixed in solution in any ratio. The solvent is driven off leaving a mixture of components A and B. In the case where one or both components are monomers, polymerization may be initiated. The result is the formation of two interpenetrating polymer networks deriving from the respective components A and B.

Solvent choice, ratio of the monomers and/or polymers, initiator and polymerization rates all play roles in controlling the morphology of the IPN, and these factors may be employed to achieve a high degree of control of the IPN morphology.

If polymer A (formed from a monomer, or provided in polymerized form) is mechanically stable, then polymer B may be dissolved or etched away to leave a high surface area network of only polymer A. For example, slightly acidic (by addition of $HNO_3$) tetraethylorthosilicate (TEOS), 5 w/w % in methanol, mixed with polystyrene sulfonic acid (PSSA), 5 w/w % in methanol, in equal parts, may be spin-, dip-, or spray-coated on a surface to form a thin film. Upon hydrolysis of the TEOS, an IPN has formed. Exposure of the IPN to a hydrogen fluoride (HF) environment etches away the $SiO_2$ formed by TEOS hydrolysis, to leave an exposed PSSA network.

The resulting thin film exposed polymer network may be used for adsorption of gases on delicate analytical devices such as quartz crystal microbalances where thin films are required so that the device may oscillate near its fundamental frequency. Other potential uses include backfilling the porous network (which may be ionically or electrically conductive) with a second conductive component (ionic if the existing component is electrically conductive, and vice versa) so as to create a composite electrode for use in batteries or fuel cells.

Although described above with reference to a two-component IPN, it will be appreciated that the invention may be practiced with other and different numbers of monomers and/or polymers. For example, a three component IPN may be formed, following the formation of which the network is processed to partially remove each of two or more components of the network, to form a porous network.

As a further alternative, a polymer film may be formed of a single polymer component, followed by treatment to partially remove the polymer, e.g., by a treatment that will selectively attack or solubilize moieties of the polymer so that it is degraded to yield a porous polymeric residue from the film of starting material.

Figure 6:
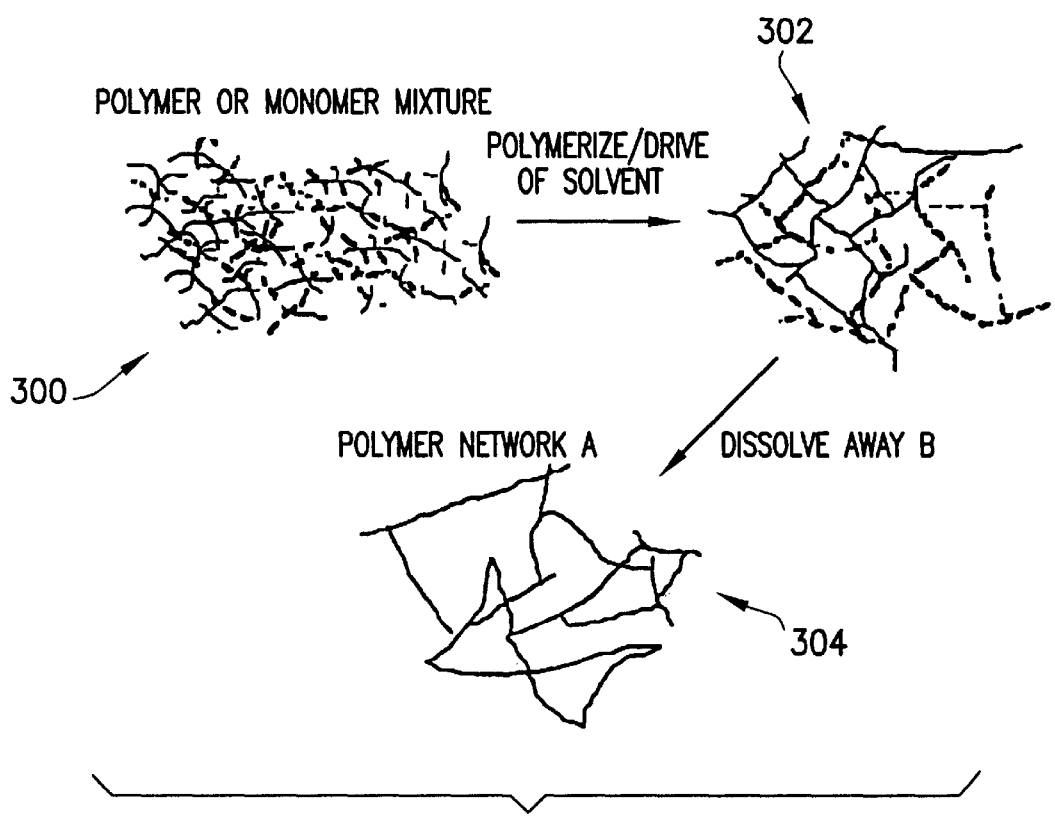
FIG. 6 is a schematic depiction of the formation of a porous network structure according to another embodiment of the invention.

FIG. 6 is a schematic depiction of the formation of a porous network structure according to another embodiment of the invention. As illustrated, a polymer and/or monomer mixture 300 is provided comprising for example a mixture of monomers A and B in a suitable solvent medium, e.g., a multi-component solvent mixture. The mixture of monomers then may be subjected to polymerization conditions, to polymerize the respective monomers A and B to form poly-A and poly-B, and at the same time to drive off the solvent. For example, the monomer mixture may contain free radical initiator species, which in exposure to ultraviolet radiation initiate free-radical polymerization species.

The resulting film of poly-A and poly-B form an IPN 302.

The IPN 302 then is washed with a solvent that solvates the IPN film to selectively dissolve away poly-B, leaving the porous poly-A material 304. Such poly-A material 304 thus may form a film of suitable porosity that is selective for adsorption of a desired gas component of a gas mixture when the porous poly-A film is formed on the surface of a piezoelectric crystal. Alternatively, the porous poly-A material film may be utilized as a matrix having dispersed therein an active sorbent or scavenger component having affinity for a specific component of a multi-component gas mixture to be monitored in the operation of a process or the operation of an environmental gas sensing system.

While the invention has been described herein with reference to specific aspects, features, and embodiments, it will be apparent that other variations, modifications, and embodiments are possible, and all such variations, modifications, and embodiments therefore are to be regarded as being within the spirit and scope of the invention.

What is claimed is:

1. A sensor assembly for detecting the presence of a gas species in a gaseous environment susceptible to the presence of the gas species, said sensor assembly comprising:
   a dynamic housing comprising at least one chamber;
   a piezoelectric crystal coated with a sensor material, wherein said sensor material has a sorptive affinity for a species of the gaseous environment, wherein the piezoelectric crystal is arranged to interact with the gaseous environment in monitoring a compositional character of the gaseous environment, and wherein said dynamic housing shields said sensor material from unwanted molecular species.

2. The sensor assembly of claim 1, wherein the piezoelectric crystal is coated with a sensor material selected from the group consisting of polystyrene sulfonic acid, polyvinylchloride vinyl acetate copolymer, siloxane and polyethylene oxide.

3. The sensor assembly of claim 1, wherein two or more chambers each contain a piezoelectric crystal having a different sorptive interaction with the gaseous environment in exposure thereto.

4. The sensor assembly of claim 3, wherein the piezoelectric crystal in a first chamber is maintained at a different condition than a piezoelectric crystal in a second chamber, whereby each of such crystals may be contacted with the gaseous environment at a different condition to provide a differential response to the gaseous environment, for quantitation of a species of the gaseous environment.

5. The sensor assembly of claim 4, wherein said different condition is a different temperature condition.

6. The sensor assembly of claim 4, wherein said different condition is a different pressure condition.

7. The sensor assembly of claim 3, wherein a piezoelectric crystal in a first chamber is coated with a sensor material comprising polystyrene sulfonic acid, and a piezoelectric crystal in a second chamber is coated with a sensor material comprising a polyvinylchloride vinyl acetate copolymer.

8. The sensor assembly of claim 1, further comprising electric oscillator circuitry for applying an oscillating electric field to the piezoelectric crystal to generate an output frequency therefrom indicative of the presence of a gas species of interest when present in said gaseous environment and when said gas environment is contacted with the piezoelectric crystal.

9. A method of detecting the presence of a gas species in a gaseous environment susceptible to the presence of the gas species, said method comprising the steps of:

contacting the gaseous environment with a sensor assembly comprising:

a dynamic housing that includes at least one chamber containing a piezoelectric crystal coated with a sensor material, wherein said sensor material has a sorptive affinity for a species of the gaseous environment, wherein the piezoelectric crystal is arranged to interact with the gaseous environment in monitoring a compositional character of the gaseous environment; and preventing an unwanted molecular species from contacting said sensor material.

10. The method of claim 9, further comprising applying an oscillating electric field to the piezoelectric crystal to generate an output frequency therefrom indicative of the presence of a gas species when present in said gas environment and when said gas environment is contacted with the piezoelectric crystal.

11. The method of claim 9, further comprising (i) applying an oscillating electric field to the piezoelectric crystal to generate an output resonant frequency therefrom, (ii) sampling the output resonant frequency of the piezoelectric crystal while said oscillating electric field is applied thereto, (iii) determining the change in resonant frequency incident to the reaction of the sensor material with a gas species, and (iv) generating an output indicative of the presence of a gas species in the gaseous environment.

12. The method of claim 9, wherein the piezoelectric crystal is coated with a sensor material selected from the group consisting of polystyrene sulfonic acid, polyvinylchloride vinyl acetate copolymer, siloxane and polyethylene oxide.

13. The method of claim 9, wherein the piezoelectric crystal exhibits a frequency response rate in the range of from about 0.001 to about 100,000 milliHertz/min/(part-per-million of said gas species) to a gas species, wherein said gas species is selected from the group consisting of HF, SiF4 and NF3.

14. The method of claim 9, wherein the piezoelectric crystal exhibits a frequency response rate in the range of from about 1 to about 5000 milliHertz/min/(part-per-million of said gas species) to a gas species, wherein said gas species is selected from the group consisting of HF, SiF4 and NF3.

15. The method of claim 9, wherein the piezoelectric crystal has a fundamental resonant frequency in the range of from 1 Megahertz to 20 Megahertz.

16. The method of claim 9, wherein the gaseous environment comprises an effluent gas stream from a high temperature composite manufacturing system including an atmospheric pressure chemical vapor deposition reactor arranged for atmospheric chemical vapor deposition of ceramic coatings on reinforcement yarns to produce high temperature composite articles.

17. The method of claim 16, wherein a piezoelectric crystal in a first chamber is coated with a sensor material comprising siloxane, and a piezoelectric crystal in a second chamber is coated with a sensor material comprising polyethylene oxide.

* * * * *